US006616556B1

(12) United States Patent
Osmudsen

(10) Patent No.: US 6,616,556 B1
(45) Date of Patent: Sep. 9, 2003

(54) METHOD AND APPARATUS FOR MEASURING LEG DRIVE

(76) Inventor: Alan Osmudsen, 56 Station Ave., Staten Island, NY (US) 10309

( * ) Notice: Subject to any disclaimer, the term of this patent is extended or adjusted under 35 U.S.C. 154(b) by 0 days.

(21) Appl. No.: 09/991,279

(22) Filed: Nov. 16, 2001

(51) Int. Cl.[7] .......................... A63B 69/00; A63B 53/06; A63B 71/00; A63D 9/00
(52) U.S. Cl. ...................... 473/452; 473/497; 473/500; 473/269; 473/218
(58) Field of Search .............................. 473/150–156, 473/218, 269, 452, 497, 499–501

(56) References Cited

U.S. PATENT DOCUMENTS

| | | | | |
|---|---|---|---|---|
| 4,577,868 A | * | 3/1986 | Kiyonaga | 473/269 |
| 5,000,449 A | * | 3/1991 | Weeks | 473/452 |
| 5,150,902 A | * | 9/1992 | Heisler | 473/269 |
| 5,577,916 A | * | 11/1996 | Gordon | 434/252 |
| 5,945,610 A | * | 8/1999 | Galasso | 73/862.042 |
| 6,039,658 A | * | 3/2000 | Cecchin | 473/269 |
| 6,139,450 A | * | 10/2000 | Rivers | 473/422 |
| 6,386,996 B1 | * | 5/2002 | Foster | 473/452 |
| 6,422,872 B1 | * | 7/2002 | Outlaw | 434/247 |

* cited by examiner

*Primary Examiner*—Paul T. Sewell
*Assistant Examiner*—Mitra Aryanpour
(74) *Attorney, Agent, or Firm*—Daly, Crowley & Mofford, LLP

(57) ABSTRACT

An apparatus to measure leg drive of a pitcher as the pitcher as delivering a pitch is presented. The device comprises a pressure gauge integrated into a pitching rubber to provide a pressure profile of the leg drive utilized by the pitcher during delivery of a pitch. This device would be useful in evaluating pitchers, in determining if a pitcher has recovered from injury, to determine if a pitcher is tiring during a game, and to provide a general indication of the pitchers ability to throw hard. The device could also be used a training device, and used to coach pitchers into developing a strong leg drive. The device may further be used in conjunction with additional sensors to determine the turnover ratio of a pitcher, the time from when the front foot hits the front of the mound to when the back foot comes off the pitching rubber.

11 Claims, 2 Drawing Sheets

METHOD AND APPARATUS FOR MEASURING LEG DRIVE

CROSS REFERENCE TO RELATED APPLICATIONS

Not Applicable.

STATEMENT REGARDING FEDERALLY SPONSORED RESEARCH

Not applicable

FIELD OF THE INVENTION

The present invention relates generally to a device for measuring leg drive and more particularly for a device for measuring leg drive of a pitcher as the pitcher delivers a pitch.

BACKGROUND OF THE INVENTION

Baseball pitchers vary in size and in the speed of the pitches they throw. There is no direct correlation between the size of a pitcher and how hard the pitcher throws. For example, Pedro Martinez is relatively small in stature, yet throws the ball much harder than other pitchers who are much bigger physically than him.

Radar guns have been used to determine the speed of a pitched ball, but do not relate to why or how the pitch was delivered at that speed. A common thought is that leg drive is an important factor in delivering a pitch, and that pitchers with a strong leg drive, regardless of the size of the pitcher, will throw harder than pitchers without a strong leg drive.

U.S. Pat. No. 5,150,902 to Heisler describes a pair of detectors for sensing a weight distribution during a golf swing or a baseball swing. This device however only measures weight in a vertical direction, and thus does not describe or suggest the measurement of leg drive, which involves a horizontal pressure component. The Heisler device could not be used to measure leg drive of a pitcher or other athlete during the act of throwing. U.S. Pat. No. 6,039,658 to Cecchin and U.S. Pat. No. 5,945,610 to Galasso describe similar devices as that of Heisler, and therefore do not provide the measurement of leg drive during the act of throwing an object. It would therefore be desirable to provide an apparatus for measuring leg drive of a person as the person is performing the act of throwing an object.

SUMMARY OF THE INVENTION

An apparatus to measure leg drive of a pitcher as the pitcher is delivering a pitch is presented. The device comprises a pressure gauge integrated into a pitching rubber to provide a pressure profile of the leg drive utilized by the pitcher during delivery of a pitch. This device is useful in evaluating pitchers and other athletes, in determining if a pitcher has recovered from injury, in determining if a pitcher is tiring during a game, and to provide a general indication of the pitchers ability to throw hard. The device could also be used as a training device, and used to coach pitchers into developing a strong leg drive. The device may further be used in conjunction with additional sensors to determine the turnover ratio of a pitcher, the time from when the pitcher's front foot hits the front of the mound to when the pitcher's back foot comes off the pitching rubber.

BRIEF DESCRIPTION OF THE DRAWINGS

The invention will be more fully understood from the following detailed description taken in conjunction with the accompanying drawings, in which.

DETAILED DESCRIPTION OF THE INVENTION

A pitching rubber is a well-known device. The pitching rubber typically measures approximately twenty-three inches long and approximately 5 inches wide and is comprised of a resilient material such as rubber. The pitching rubber is attached to the pitching mound, and is used by pitchers during the wind up and delivery to drive against with their back leg.

Figure 1:
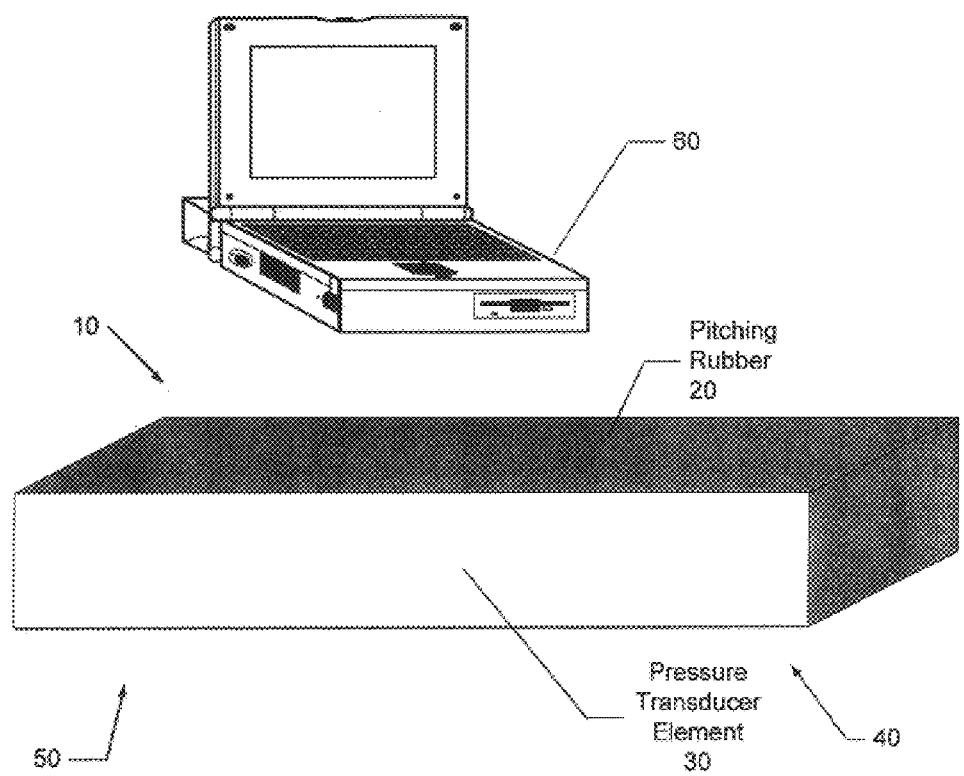
FIG. 1 is a block diagram of the present invention.

Referring now to FIG. 1, the present invention 10 is shown. The present invention comprises, in a first embodiment, a standard pitching rubber 20 that has been modified to include a pressure transducer element 30 along a front surface thereof. While the figure shows the pressure transducer element 30 extending along the entire front face of the pitching rubber, the transducer element could also extend only along a portion of the front face of the pitching rubber. The pressure transducer element 30 may comprise one or more pressure transducers, and the pressure transducers can be any kind of pressure transducer that is known in the art. Possible types of pressure transducers include electric, hydraulic, mechanical and various combinations. The purpose of the transducer element 30 is to measure the amount of pressure applied to it over a period of time.

The transducer element 30 extends along the front face of the pitching rubber 20. This is desirable since it is common for pitchers to work from a particular area of the front surface of the pitching rubber. Typically, a left-handed pitcher will tend to work from the right-hand section 40 of the front surface of the pitching rubber 20 as this tends to increase the angle between the pitcher and the batter. Similarly, right-handed pitchers tend to work from a left-hand side 50 of the front surface of the pitching rubber 20 as this increases the angle between the pitcher and the batter as well.

The transducer element 30 is shown as a single transducer, though other embodiments could include transducer element 30 as including multiple transducers disposed across the front surface of the pitching rubber, with each transducer providing a respective pressure profile. With a configuration including multiple transducers, pressure profiles relating to various portions of the pitcher's foot could be produced. For example, such a set of pressure profiles may indicate that a pitcher is pushing off more with his Display device 60 is used to provide the readings from the transducer. The display device 60 is in communication with the transducer by way of a communications link, either optical, wired, or wireless. Communications from the transducer to the display device could be via digital or analog signals. In a preferred embodiment the transducer is in wireless RF communication with the display device which is a laptop computer. The computer has software for taking the outputs from the transducer and converting them into a readout that can be utilized by the computer operator.

Figure 2:
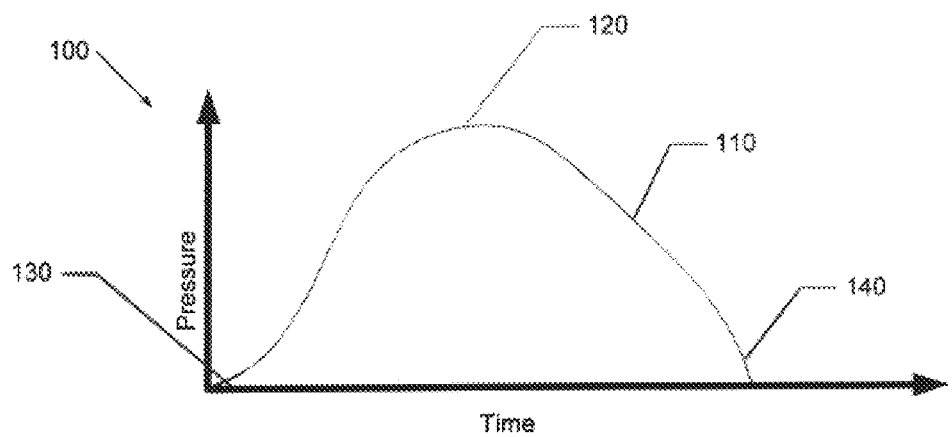
FIG. 2 is a pressure profile graph provided by the present invention.

Referring now to FIG. 2, a pressure profile 100 is shown which was achieved by way of the present invention. The pressure profile 100 has pressure for a vertical axis and time as a horizontal axis. The resulting plot 110 was recorded by the present invention during a pitcher's windup and delivery. The plot 110 is used to determine the maximum leg drive provided by the pitcher during the delivery of a pitch, shown as mark 120 on the plot. Plot 110 can also be used to measure the elapsed time from the start of the delivery 130 to the end of the delivery 140. Further the plot 110 can be used to determine the rate at which the leg drive is provided by measuring the slope of the line at various points from marks 130 to 120, and from marks 120 to 140.

Figure 3:
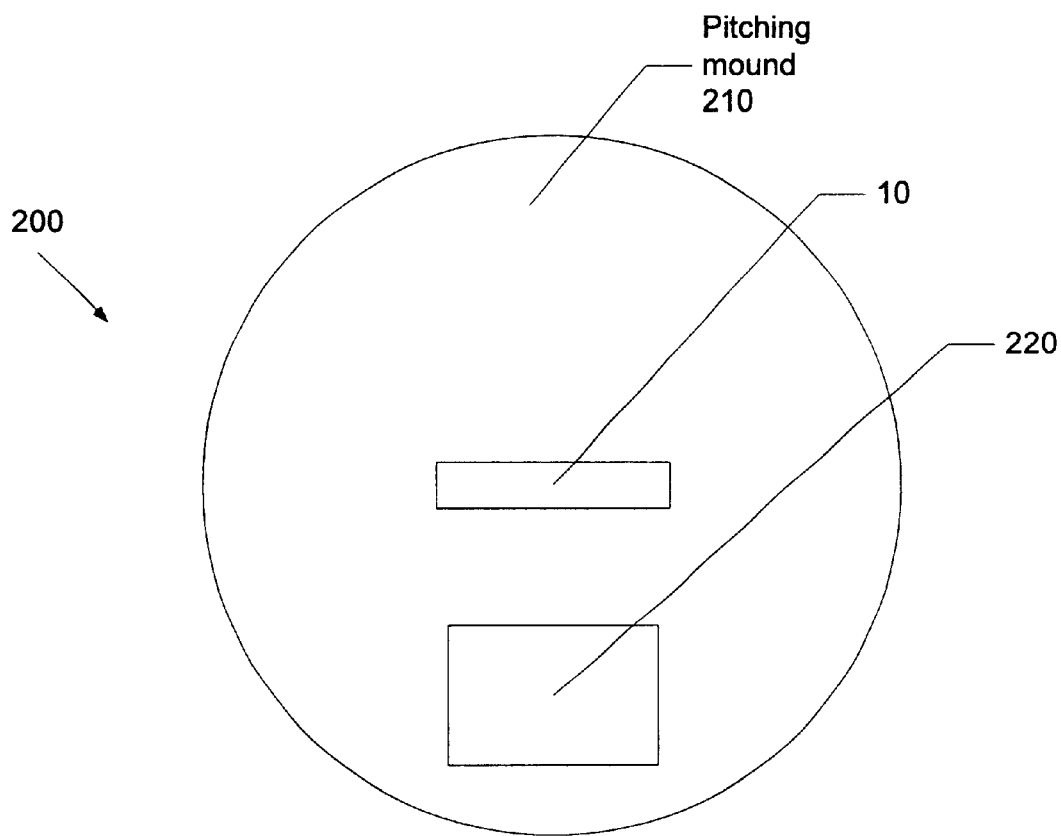
FIG. 3 is a diagram of another embodiment of the invention used to measure a pitchers turnover ratio.

FIG. 3 shows a further embodiment of the present invention. In this configuration, the pitching rubber having the pressure transducer element disposed therein is shown on a pitching mound 210. Also provided is a pressure sensitive landing mat 220. The landing mat has a similar pressure transducer element (with one or more transducers comprising this pressure transducer element as well) as that present in the pitching rubber and is used to provide additional information regarding the leg drive utilized by a pitcher. During a pitchers windup there is a transfer and drive as the pitcher strides toward home plate. There is also a turnover ratio of a pitcher, the time from when the pitcher's front foot hits the front of the mound (as detected by the pressure sensitive mat 220) to when the back foot comes off the pitching rubber, signified by the drop in pressure as seen by the pitching rubber transducer element. Not only is there a pressure transformation that can be measured, but also the timing of the entire process, and of various portions of the process, can be determined.

Figure 4:
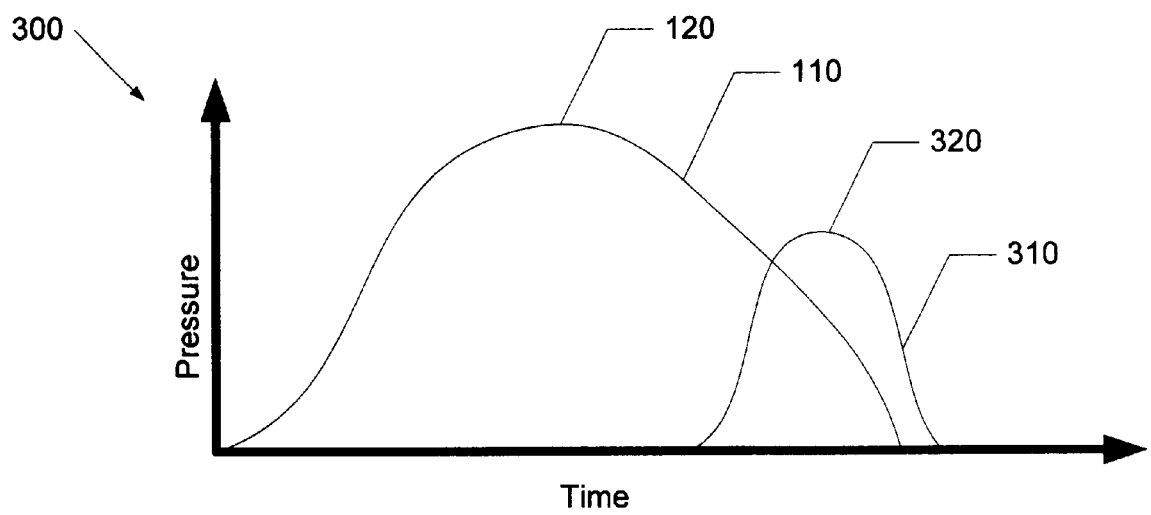
FIG. 4 is a pressure profile graph provided by the embodiment of FIG. 3.

FIG. 4 shows a pressure profile and the turnover ratio. Graph 110 is the pressure profile measured by the pitching rubber transducer element. Graph 310 is the pressure profile measured by the landing mat. As can be seen from these graphs, the timing between the peak of the first curve 120 and the peak of the second curve can be ascertained 320, as can the magnitudes of the respective peaks. In the example shown in FIG. 4, the peak of curve 310 is less than the peak of curve 110, therefore, not all of the pitchers pressure is being turned over from the back foot to the front foot during the pitchers delivery. This could be used to show the pitcher that, for example, he is not following through properly, is striding too long or too short, or any other reason which would result in the lesser amplitude of pressure profile 310.

The results achieved by way of the present invention have many uses. The device can be used as a teaching aid. The student would have a pressure profile produced by the present invention, and the profile would be analyzed to determine how the pitcher is using the leg drive. The student could be taught to utilize more leg drive, or to modify his pitching motion so that more leg drive is achieved.

The device can be used as a scouting tool to measure a pitcher's pressure profile and determine how well the pitcher is using his mechanics, including leg drive, to deliver a pitch. A pitcher who uses a strong leg drive would tend to throw harder and more importantly to put less strain on the shoulder and/or elbow, thereby having a longer career. On the other hand, a pitcher who does not have a strong leg drive may be considered a potential risk due to the strain placed on the pitcher's arm.

The invention can also be used as an indicator of how well a pitcher is recovering from injury. When the pitchers current pressure profile matches his pressure profile prior to the injury, then the pitcher can be seen to have recovered from the injury. The invention can also be used during a game to measure how tired a pitcher is getting. As a pitcher tires, his leg drive would diminish, and by way of the present invention providing a quantitative measurement, the fatigue of a pitcher can be determined quickly, effectively and accurately.

While the present invention has been described as being used with a pitcher, the device could also be used by other baseball players, both infielders and outfielders to measure the pressure profiles as they make their throws. The device also has applications to other sports, such as measuring the pressure profile of a quarterback as he throws a football, of a basketball player as he takes a shot, and the like.

Having described preferred embodiments of the invention it will now become apparent to those of ordinary skill in the art that other embodiments incorporating these concepts may be used. Accordingly, it is submitted the invention should not be limited to the described embodiments but rather should be limited only by the spirit and scope of the appended claims. All publications and references cited herein are expressly incorporated herein by reference in their entirety.

What is claimed is:

1. A measuring apparatus comprising:

a pitching rubber;

a first pressure transducer element disposed at least partially within a front surface of said pitching rubber, said first pressure transducer element capable of measuring leg drive pressure applied thereto in a generally horizontal direction by a person performing an activity; and a display device in communication with said first pressure transducer element, said display device displaying the pressure sensed by said first pressure transducer element.

2. The apparatus of claim 1 wherein said display device is located remotely from said first pressure transducer element.

3. The apparatus of claim 1 wherein said display device displays a first pressure profile from data provided by said first pressure transducer element.

4. The device of claim 1 wherein said display device comprises a computer.

5. The device of claim 1 wherein said first pressure transducer element comprises at least one pressure transducer.

6. The device of claim 5 wherein said at least one pressure transducer is selected from an electrical pressure transducer, a mechanical pressure transducer, and a hydraulic pressure transducer.

7. The device of claim 1 further comprising a second pressure transducer element, said second transducer element located remotely from said first pressure transducer element, said second pressure transducer element in communication with said display device.

8. The device of claim 7 wherein said second pressure transducer element comprises at least one pressure transducer.

9. The device of claim 8 wherein said at least one pressure transducer is selected from an electrical pressure transducer, a mechanical pressure transducer, and a hydraulic pressure transducer.

10. The device of claim 7 wherein said display device displays a second pressure profile from data provided by said second pressure transducer element.

11. The device of claim 7 wherein said second pressure transducer element is capable of measuring pressure applied thereto in a generally vertical direction by the person.

* * * * *